United States Patent [19]

Keay et al.

[11] 4,272,441

[45] Jun. 9, 1981

[54] PREPARATION OF CARBAMATES

[75] Inventors: Robert E. Keay, Stockton, N.J.; Edward F. Orwoll, Fort Littleton, Pa.; John A. Price, Kingston, N.J.

[73] Assignee: FMC Corporation, Philadelphia, Pa.

[21] Appl. No.: 129,936

[22] Filed: Mar. 13, 1980

[51] Int. Cl.$^3$ ............................................ C07D 307/86
[52] U.S. Cl. ........................ 260/346.73; 260/340.5 R; 260/340.9 R; 560/163; 560/164
[58] Field of Search ................. 260/340.5 R, 340.9 R, 260/346.73; 562/163

[56] References Cited

U.S. PATENT DOCUMENTS 4,086,246   4/1978   Toth et al. .................... 260/340.9 R

FOREIGN PATENT DOCUMENTS

78/0364   1/1978   South Africa .
1537889   1/1979   United Kingdom .

OTHER PUBLICATIONS

Chem. Week, Pesticides Register, McGraw-Hill, N.Y., N.Y., 1977.
Pesticide Index, The Entomological Soc. of America, College Park, Md. (1976).

*Primary Examiner*—Henry R. Jiles
*Assistant Examiner*—Bernard Dentz
*Attorney, Agent, or Firm*—Richard L. Hansen; Henry R. Ertelt

[57] ABSTRACT

Carbamates are prepared in one step by reacting an alcohol, phosgene, and an amine in the absence of an acid scavenger.

10 Claims, No Drawings

PREPARATION OF CARBAMATES

BACKGROUND OF THE INVENTION

This invention is in the field of chemical processes; more specifically, this invention is an improvement in a known process for making carbamates, organic compounds of the general formula:

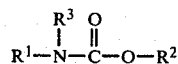

Carbamates are well known compounds having established utilities as drugs, insecticides, and as polymer precursors, for example. Carbamate insecticides are listed in various indexes; for example, "Chemical Week Pesticides Register,"McGraw-Hill Book Co., New York, N.Y., 1977 and "Pesticide Index," The Entomological Society of America, College Park, Md., 1976. Such insecticides include, for example, butacarb, carbofuran, carbaryl, terbucarb, ethiofencarb, bufencarb, isoprocarb, aminocarb, bendiocarb, dioxacarb, formetanate, methiocarb, promecarb, propoxur, dicresyl, and MPMC, which are common names for carbamates of the aforesaid formula wherein $R^1$ is methyl, $R^2$ is 3,5-di-tert-butylphenyl, 2,3-dihydro-2,2-dimethyl-7-benzofuranyl, 1-naphthyl, 2,6-di-tert-butyl-4-methylphenyl, 2-ethylthiomethylphenyl, 3-(1-methylbutyl)phenyl and 3-(1-ethylpropyl)phenyl (i.e., a mixture), 2-isopropylphenyl, 4-dimethylamino-3-methylphenyl, 2,2-dimethyl-1,3-benzodioxol-4-yl, 2-(1,3-dioxolan-2-yl)phenyl, 3-dimethylaminomethyleneiminophenyl, 3,5-dimethyl-4-(methylthio)phenyl, 3-isopropyl-5-methylphenyl, 2-(1-methylethoxy)phenyl, 3-methylphenyl, and 3,4-dimethylphenyl, respectively, and $R^3$ is hydrogen.

The aforesaid carbamates are prepared in several ways. For example, they are prepared by condensing an alcohol or phenol, $R^2OH$, with a previously prepared isocyanate, $R^1NCO$, or carbamoyl chloride, $R^1NHCOCl$, or with phosgene first and subsequent reaction of the chloroformate thus produced with an amine, $R^1NH_2$.

U.S. Pat. No. 4,086,246 discloses a process for making carbamates in one step from commercially available materials, wherein the phenol, $R^2OH$, phosgene, and an amine, $R^1NH_2$, are all reacted in a common water-immiscible organic solvent in the same reaction vessel at the same time in the presence of an acid binding agent to yield the carbamate. The acid binding agent, generally a tertiary amine, is a scavenger for the by-product hydrogen chloride.

The scavenged hydrogen chloride salt is a troublesome by-product, difficult to remove from the reaction mixture and costly to dispose of without contaminating the environment. Furthermore, in order to avoid the formation of 1,3-dimethylurea, the prior art has employed large amounts of phosgene, creating further separation and disposal problems as well as higher costs. Thus, the aforesaid requirements in the one-step process of the prior art seriously limit the commercial utility of that process. The economic advantage of a one-step process over two steps via an isocyanate, carbamoyl chloride, or chloroformate intermediate will be evident.

SUMMARY OF THE INVENTION

According to this invention, neither an acid scavenger nor substantial excess phosgene are required, thereby avoiding the above-cited disadvantages of the known one-step process and providing an economically and environmentally attractive method to prepare carbamates.

This invention is a process for making a carbamate of the formula

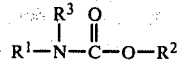

wherein $R^1$, $R^2$, and $R^3$ can be any substituent organic radicals or groups which are not detrimentally affected by the process, and $R^3$ can also be hydrogen, which comprises adding phosgene and an amine, $R^1NHR^3$, to an alcohol or phenol, $R^2OH$, in a water-immiscible organic solvent in the absence of an acid binding agent.

In terms of the prior art one-step process for making compounds of the formula

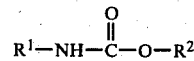

wherein $R^1$ is alkyl, alkyl substituted by halogen, alkyl substituted by alkoxy, aryl, aryl substituted by halogen, aryl substituted by alkyl, aryl substituted by alkoxy, aralkyl, aralkyl substituted by halogen, aralkyl substituted by alkyl, aralkyl substituted by alkoxy, cycloalkyl substituted by halogen, cycloalkyl substituted by alkyl or cycloalkyl substituted by alkoxy, and $R^2$ is an aromatic group, an aromatic group substituted by alkyl, an aromatic group substituted by halogen, an aromatic group substituted by alkoxy, a heteroaromatic group, a heteroaromatic group substituted by alkyl, a heteroaromatic group substituted by halogen, or a heteroaromatic group substituted by alkoxy, by the reaction of phosgene with a phenol of the formula:

and further by reaction of a primary amine of the formula:

by reacting all three of the above-mentioned reactants in a common water-immiscible organic solvent in the same reaction vessel at the same time in the presence of an acid binding agent, this invention is the improvement which comprises omitting the acid binding agent.

Among the carbamates which are produced by this invention, it is preferred that the process be employed to make those insecticidal carbamates wherein $R^1$ is methyl, and $R^2$ is selected from 3,5-di-tert-butylphenyl, 2,3-dihydro-2,2-dimethyl-7-benzofuranyl, 1-naphthyl, 2,6-di-tert-butyl-4-methylphenyl, 2-ethylthiomethylphenyl, 3-(1-methylbutyl)phenyl, 3-(1-ethylpropyl)phenyl, 2-isopropylphenyl, 4-dimethylamino-3-methylphenyl, 2,2-dimethyl-1,3-benzodioxol-4-yl, 2-(1,3-dioxolan-2-yl)phenyl, 3-dimethylaminomethyleneiminophenyl, 3,5-dimethyl-4-(methylthio)phenyl, 3-isopropyl-5-methylphenyl, 2-(1-methylethoxy)phenyl, 3-methylphenyl, and 3,4-dimethylphenyl. Further, it is most preferred that $R^2$ be selected from 2,3-dihydro-2,2-dimethyl-7-benzofuranyl, 1-naphthyl, 3,4-dimethylphenyl, and 3-methylphenyl. The process of this invention is most especially preferred in the case that $R^1$ is methyl, $R^2$ is 2,3-dihydro-2,2-dimethyl-7-benzofuranyl and the product is carbofuran.

DETAILED DESCRIPTION

Various water-immiscible organic solvents may be employed in the process, but it is preferred that aprotic solvents, such as hydrocarbons, be used. For example, aliphatic hydrocarbons, such as hexane, cyclohexane, heptane, and octane, and aromatic solvents, such as benzene, toluene, xylene, and mesitylene, as well as halogen-substituted analogs of any of these, can be used. Toluene is the preferred solvent when the process is used to prepare carbofuran.

Although the process may be conducted at temperatures in the range 50°–150° C., temperatures between 85° C. and 125° C. are preferred.

In carrying out the process, the phosgene and amine are added at the same time, i.e. concurrently, but as separate streams, to the stirred $R^2OH$ and solvent. It is further preferred that the addition be done gradually. The term, "gradually," herein means not all at once, but over the course of the reaction, either continuously or discontinuously.

The course of the reaction is followed conveniently by gas chromatography or by monitoring the evolution of HCl; for example, by trapping the evolved HCl in a standardized NaOH solution and back titrating; two moles of HCl are evolved for every mole of $R^2OH$ reacted to form carbamate.

The process of making carbamate formally requires equimolar amounts of amine, $R^2OH$, and phosgene, but it is preferred to employ a slight excess of phosgene, to about a 20% molar excess of phosgene over amine. Very close to equimolar amounts of amine and $R^2OH$ are preferred in general.

It is especially preferred, however, in making carbofuran, to terminate the reaction before all of the 2,3-dihydro-2,2-dimethyl-7-benzofuranol has reacted. As complete conversion of the benzofuranol is approached, the following side reaction, producing an allophanate and consuming the desired product, becomes more pronounced.

$R^1NHCOOR^2 + COCl_2 + R^1NH_2 \rightarrow R^1NHCONR^1COOR^2 + HCl$

Thus, it is desirable to monitor the reaction mixture, e.g., with gas chromatography. When the allophanate concentration is about 1–20%, preferably about 2–5%, of the carbofuran concentration, the reaction is terminated by stopping the addition of phosgene and methylamine. At such termination, the conversion of 2,3-dihydro-2,2-dimethyl-7-benzofuranol is generally about 80%. The crystalline carbofuran is isolated by filtration, and the filtrate, containing unreacted 2,3-dihydro-2,2-dimethyl-7-benzofuranol, is recycled as the solvent in a subsequent batch run. In this way the overall yield is improved.

The manner in which the process of this invention is carried out is illustrated in the following Examples, the specific details of which should not be regarded as limitations.

EXAMPLE 1

PREPARATION OF CARBOFURAN

A stirred solution of 2,3-dihydro-2,2-dimethyl-7-benzofuranol (100.0 g, 0.6 mole) in 500 g of toluene was heated to 95° C. under nitrogen. Gaseous phosphene (approximately 15 g/hr) and monomethylamine (approximately 3–4 g/hr) were metered into the flask concurrently and gradually until gas chromatographic analysis indicated that the amount of allophanate by-product was 3% of the carbofuran present. At this point, the addition of phosgene and monomethylamine was stopped, but heating was continued for 1.25 hours to ensure complete reaction. In this run, the point at which the reaction was terminated corresponded to the addition of 73.0 g (0.74 mole) of phosgene and 19.0 g (0.61 mole) of monomethylamine, which resulted in an 80% conversion of 2,3-dihydro-2,2-dimethyl-7-benzofuranol and a 73% yield of carbofuran. After a total reaction time of 5.75 hours, the reaction mixture was filtered hot. After cooling the filtrate to room temperature, the carbofuran which had crystallized was isolated by filtration and dried. The dried carbofuran weighed 79.5 g and was assayed to be 98% pure, representing a 60% isolated yield. The filtrate was then recycled in the next carbamoylation run.

The same procedure was used for runs 2 through 10 in in which the filtrate was similarly recycled. Data appear in Table I. The overall yield of carbofuran having a purity of 95–98% was 90%.

TABLE I

| | $R^2OH$ | | | | | | $R^2OH$ | Yield Carbo- |
|---|---|---|---|---|---|---|---|---|
| Run | Total (mole)[1] | Fresh (mole) | $COCl_2$ (mole) | $CH_3NH_2$ (mole) | Time (hr) | Temp. (°C.) | Conver. (%) | furan (%) |
| 1 | 0.60 | 0.60 | 0.74 | 0.61 | 5.75 | 95 | 80 | 73 |
| 2 | 0.61 | 0.48 | 0.72 | 0.55 | 5.0 | 96 | 77 | 69 |
| 3 | 0.62 | 0.48 | 0.73 | 0.52 | 4.5 | 96 | 76 | 66 |
| 4 | 0.63 | 0.46 | 0.73 | 0.63 | 5.75 | 97 | 75 | 63 |
| 5 | 0.60 | 0.43 | 0.70 | 0.48 | 4.5 | 96 | 78 | 70 |
| 6 | 0.59 | 0.49 | 0.67 | 0.54 | 4.5 | 97 | 78 | 63 |
| 7 | 0.61 | 0.48 | 0.72 | 0.61 | 5.0 | 97 | 80 | 70 |
| 8 | 0.60 | 0.46 | 0.75 | 0.64 | 5.5 | 96 | 80 | 65 |
| 9 | 0.59 | 0.46 | 0.77 | 0.48 | 5.0 | 97 | 85 | 73 |
| 10 | 0.59 | 0.49 | 0.75 | 0.52 | 4.5 | 97 | 80 | 76 |

[1]Includes unreacted $R^2OH$ from previous run.

EXAMPLE 2

PREPARATION OF CARBARYL

A stirred solution of 1-naphthol (86.5 g, 0.6 mole) in 500 g of toluene was heated under nitrogen to 98° C. Phosgene (79.9 g, 0.8 mole) and methylamine (22.0 g, 0.7 mole) were then metered into this solution concurrently and gradually over a period of approximately 6.5 hours. The reaction mixture was filtered hot. The filtrate was then allowed to cool to room temperature, and the crystallized carbaryl was recovered by filtration. The yield of 1-naphthyl methylcarbamate was 78%.

EXAMPLE 3

PREPARATION OF 3,4-DIMETHYLPHENYL METHYLCARBAMATE

A solution of 3,4-dimethylphenol (73.3 g, 0.600 mole) in 500 g of toluene was heated under nitrogen to 99° C. Phosgene (71 g, 0.72 mole) and methylamine (20 g, 0.64 mole) were metered into the stirred solution as gases concurrently and gradually over a period of four hours, while the temperature was maintained at 97°–99° C. After an additional half hour at the same temperature, the hot mixture was filtered; the filtrate was concentrated to yield 102.7 g of an oil which contained 3,4-dimethylphenyl methylcarbamate in a 70% yield.

EXAMPLE 4

PREPARATION OF 3-METHYLPHENYL METHYLCARBAMATE

A solution of 3-methylphenol (64.9 g, 0.600 mole) in 500 g of toluene was heated under nitrogen to 95° C. Phosgene (76.0 g, 0.77 mole) and methylamine (16.0 g, 0.52 mole) were metered into the stirred solution as gases concurrently and gradually over a period of 4.5 hours, while the temperature was maintained at 96°–98° C. After an additional half hour at the same temperature, the hot mixture was filtered; the filtrate was concentrated to yield 103.5 g of an oil which contained 3-methylphenyl methylcarbamate in a 78% yield.

We claim:

1. In a process for making compounds of the formula $$R^1-NH-\underset{\underset{O}{\|}}{C}-O-R^2$$

wherein
R$^1$ is alkyl, alkyl substituted by halogen, alkyl substituted by alkoxy, aryl, aryl substituted by halogen, aryl substituted by alkyl, aryl substituted by alkoxy, aralkyl, aralkyl substituted by alkoxy, cycloalkyl, cycloalkyl substituted by halogen, cycloalkyl substituted by alkyl or cycloalkyl substituted by alkoxy, and
R$^2$ is an aromatic group, an aromatic group substituted by alkyl, an aromatic group substituted by halogen, an aromatic group substituted by alkoxy, a heteroaromatic group, a heteroaromatic group substituted by alkyl, a heteroaromatic group substituted by halogen, or a heteroaromatic group substituted by alkoxy, by the reaction of phosgene with a phenol of the formula $$R^2-OH$$

and further by reaction of a primary amine of the formula $$R^1-NH_2$$

by reacting all three of the above-mentioned reactants in a common water-immiscible organic solvent in the same reaction vessel at the same time in the presence of an acid binding agent, the improvement which comprises omitting the acid binding agent and gradually adding the phosgene and primary amine concurrently, but as separate streams, to the stirred R$^2$—OH and solvent.

2. The process of claim 1 wherein R$^1$ is methyl and R$^2$ is selected from 3,5-di-tert-butylphenyl, 2,3-dihydro-2,2-dimethyl-7-benzofuranyl, 1-naphthyl, 2,6-di-tert-butyl-4-methylphenyl, 2-ethylthiomethylphenyl, 3-(1-methylbutyl)phenyl, 3-(1-ethylpropyl)phenyl, 2-isopropylphenyl, 4-dimethylamino-3-methylphenyl, 2,2-dimethyl-1,3-benzodioxol-4-yl, 2-(1,3-dioxolan-2-yl)-phenyl, 3-dimethylaminomethyleneiminophenyl, 3,5-dimethyl-4-(methylthio)phenyl, 3-isopropyl-5-methylphenyl, 2-(1-methylethoxy)phenyl, 3-methylphenyl, and 3,4-dimethylphenyl.

3. The process of claim 2 wherein R$^2$ is selected from 2,3-dihydro-2,2-dimethyl-7-benzofuranyl, 1-naphthyl, 3,4-dimethylphenyl, and 3-methylphenyl.

4. The process of claim 3 wherein R$^2$ is 2,3-dihydro-2,2-dimethyl-7-benzofuranyl and the product is carbofuran.

5. The process of claim 4 wherein the reaction is terminated before complete conversion of the 2,3-dihydro-2,2-dimethyl-7-benzofuranol, the carbofuran is isolated by filtration, and the filtrate is recycled in a subsequent batch.

6. The process of claim 5 wherein the waterimmiscible organic solvent is toluene.

7. The process of claim 6 conducted at a temperature of 85° C.–105° C.

8. The process of claim 1 wherein the waterimmiscible organic solvent is selected from hexane, cyclohexane, heptane, octane, benzene, toluene, xylene, and mesitylene.

9. The process of claim 1 conducted at a temperature of 50° C.–150° C.

10. The process of claim 1 wherein up to about a 20 percent molar excess of phosgene over R$^1$NH$_2$ is employed.

* * * * *